United States Patent [19]
Gorio et al.

[11] Patent Number: 5,116,873
[45] Date of Patent: May 26, 1992

[54] DRUG ACTIVE IN RESTORING NEURONAL PLASTICITY

[76] Inventors: Alfredo Gorio, via G.B. Pergolesi 7, Milano, Italy, 20124; Enrico Genazzani, via Della Maddalena 102, Revigliano (Torino), Italy

[21] Appl. No.: 629,642

[22] Filed: Dec. 7, 1990

[30] Foreign Application Priority Data

Dec. 14, 1989 [IT] Italy .................. 48660 A/89

[51] Int. Cl.$^5$ .......................................... A61K 31/195
[52] U.S. Cl. .................................................. 514/567
[58] Field of Search ........................................ 514/567

[56] References Cited

PUBLICATIONS

Schiaffino et al., 1980, Chem. Abs. 93(15):146947f, Myosin Polymorphism, Cellular Heterogeneity and Elasticity of Cardiac Muscle.
The Journal of Clinical Psychiatry, vol. 47, No. 2, 1986, p. 100; C. A. Peabody et al.: "Progressive dementia associated with thyroid disease" *The whole article*.
Arzneimittel-Forschung, vol. 31, No. 3, 1981, pp. 437–441; G. Schneider et al.: "Untersuchungen zur symptomatischen Pharmakotherapie eines moglichen Thermodells fur die Chorea Huntington" *Abstract p.441, par. 4.
Reprod. Nutr. Develop. vol. 22, No. 1B, 1982, pp. 201–208; C. Legrand et al.: "Influence of altered thyroid and nutritional states on early histoganosis of the rat cerehellar cortex with special reference to synaptogenesis" *Summary; discussion p. 206*.
Biological Reviews, vol. 54, No. 2, 1979, pp. 155–197; J. A. Kiernan: "Hypotheses concerned with axonal regeneration in the mammalian nervous system"*p. 163, par. 3-p. 164, par. 3; p. 185, summary paragraph 5*.
W. Forth et al.: "Pharmakologie und Toxikologie" 4th edition, 1983 pp. 392–393, Bibliographisches Institut AG, Zurich, CH *p. 392, last paragraph—p. 393, paragraph 1*.
Development Brain Research, vol. 36, 1987, pp. 109–120; M. Hayashi et al.: "An interaction between thyroid hormone and nerve growth factor in the regulation of choline acetyltransferase activity in neuronal cultures, derived from the septal-diagonal band region of the embryonic rat brain" *Abstract; pp. 109–110, paragraph: Introduction: p. 117, par. 2: Discussion; p. 118, par. 5, 6.

*Primary Examiner*—Stanley J. Friedman
*Attorney, Agent, or Firm*—Oblon, Spivak, McClelland, Maier & Neustadt

[57] ABSTRACT

Oral or parenteral administration of thyroid hormone T$_4$ (from 0.5 to 2 μg/100 g of body weight) stimulates, normalizes dopaminergic innervation in the corpus striatum (striate body), and restores neurochemical compensation following denervation of selective brain areas, thereby increasing neuronal plasticity.

5 Claims, No Drawings

DRUG ACTIVE IN RESTORING NEURONAL PLASTICITY

The present invention concerns the use of the thyroid hormone $T_4$ (thyroxine, tetraiodothyroxine) and pharmaceutical formulations containing said hormone, for the restoration of neuronal plasticity.

For the purpose of the present invention, neuronal plasticity is taken to mean the collective physiological, biochemical and anatomic mechanisms that allow development of the nervous system during the embryonic and postnatal periods and that, in the adult animal, is the basis of regenerative mechanisms for damaged neurons and of the adaptive capability of the central nervous system when some parts of it degenerate and can not regenerate.

Therefore, the following processes occur in order to achieve neuronal plasticity: denervation, reinnervation, synaptogenesis, synaptic repression, synaptic expansion, the sprouting of axons, neural regeneration, development and organisation of neural paths and circuits to replace the damaged ones.

Therefore, the suitable patients to be treated with the thyroid hormone $T_4$ according to the present invention are patients afflicted with degenerative pathology of the central nervous system (senile dementia like Alzheimer's disease, Parkinsonism, Huntington's chorea, cerebellar-spinal adrenoleucodystrophy), trauma and cerebral ischemia.

The thyroid hormone $T_4$ has (like the other thyroid hormone $T_3$, triiodothyroxine) two principal physiological effects: it increases protein synthesis in nearly every tissue, influencing the synthesis of mRNA; and it elevates the consumption of $O_2$. This last effect leads to a rise in the activity of $Na^+-K^+$ ATPases (sodium pump), mainly in the tissues responsible for the basal consumption of $O_2$ (i.e. liver kidneys, heart and skeletal muscle).

The only therapeutic use to which thyroid hormones are put presently is replacement therapy for hypothyroidism and myxoedema coma. The purpose of the therapy lies in restoring the level of thyroid hormones in the tissues.

Various thyroid hormone preparations exist which are suitable for replacement therapy; these include synthetic preparations of thyroxine, triiodothyroxine, mixtures of the two synthetic hormones, and dried animal thyroids.

Preferred are the synthetic preparations of L-thyroxine: the average maintenance dosage is from 150 to 200 $\mu$g/day, administered orally. When $T_4$ is administered, $T_3$ is formed via deiodination in the tissues, in order to maintain adequate serum concentrations of both hormones.

The therapy for mixoedema coma entails the use of high doses of $T_4$ administered intravenously (500 $\mu$g per intravenous bolus). The maintenance dose for $T_4$ is 50 $\mu$g intravenously per diem until such time as the hormone cannot be administered orally.

Recently [Acta Psychiatr. Scand., 76: 158-163 (1987)] some studies were conducted to clarify possible changes in thyroid function in patients suffering from Alzheimer's disease. In fact, since the histopathology of Alzheimer's disease was also localised in the hypothalamus that exerts a dominant stimulatory effect on the synthesis and secretion of thyroid-stimulating hormone (TSH), it was postulated that hypothalamic-hypophysic-thyroid function can be altered in this disease. However, the results of this study indicated the relative normality of neuroendocrine function, particularly thyroid function, in these patients.

In Neuroscience 19(4): 1207-1216 (1986), A. Rami et al. showed that reduced levels or total lack of thyroid hormone during the neonatal period reduced the acquisition of neurones in those zones in which neurogenesis occurs postnatally. For example, this seems to take place in the granular cells of the cerebellum, and in a similar way for neurones of the gyrus dentatus of the hippocampus. In this last case, it was proposed that the effect of the lack of thyroid hormone is manifested more on the cellular migration from the germinal site to the final anatomic site than on reduced neurogenesis. Moreover, the same authors showed an altered maturation of pyramidal cells [Neuroscience 19(4): 1217-1226 (1986)]. In the work published in Int. J. Dev. Neurosci., 7: 301-308, a reduced neonatal development of the enzyme AChE (acetylcholinesterase) in the hippocampus was indicated.

According to the present invention, the utility of exogenous administration of thyroid hormone $T_4$ is predicated upon the demonstration that in the corpus striatum (striate body) thyroid hormone stimulates and normalises dopaminergic innervation, thereby reducing metencephalinergic hyperinnervation caused by perinatal morphine abuse, thus showing an effect on the neuronal plasticity of dopaminergic nerve fibres.

The efficacy of the treatment with $T_4$ on neuronal plasticity was evaluated using a model in which the experimental animals (pregnant rats) were treated in the perinatal phase with morphine in order to modify their neuronal plasticity. The principal area of the brain affected by the treatment with morphine is the caudate nucleus.

Pregnant Sprague-Dawley rats (Charles River, Como, Italy) weighing about 250 g were utilised. The rats were free to drink water supplemented with morphine, that was absorbed increasingly with time (FIGS. 1, 2). In the graphs, after the birth of the little rats, the consumption of water and morphine is always referred to that of the mothers. After 21 days of life, consumption was referred directly to the little rats. As shown in the graphs, the little rats were examined at various times after birth.

Morphine chloride was administered to the animals in controlled dosages in the amount of drinking water that would be consumed within a 24 hours period. The opiate was administered to pregnant mothers from the first day of pregnancy, in increasing doses starting with 2.5 mg/day, then increased to 4 mg/day on the seventh day, to 15 mg/day on the thirteenth day and 15 mg/day from day 19 until birth. Starting from the ninth day post-partum the dose was increased gradually until it reached the maximal value of 23 mg/day on the twenty-first day. On the twenty-sixth day after birth the infant animals were put in individual cages and the daily dosage of morphine was decreased to 2.5 mg/day. Such doses were increased further as described above.

The blood levels of $T_4$ in neonates exposed perinatally to morphine are significantly reduced from the day of birth until day 30 of life, at which time one observes a normalisation of the values, as shown in the following Table I.

TABLE 1

| Blood levels of $T_4$ (ng/mL plasma) in neonates exposed perinatally to morphine | |
|---|---|
| control | morphine |
| day 1 | 8.0 ± 0.3 | 6.0 ± 0.2* |
| day 4 | 15.2 ± 0.4 | 11.3 ± 0.6* |
| day 12 | 32.6 ± 2.1 | 21.1 ± 2.6* |
| day 30 | 28.5 ± 1.6 | 27.5 ± 1.9 |

The subcutaneous administration of $T_4$ in amounts of 0.5–2 µg/100 g during the first two weeks can normalise cerebral development and the processes of neuronal plasticity selectively altered by perinatal exposure to morphine, as exemplified hereinabove.

The pharmacological effect of the exogenous administration of $T_4$ also extends to the repair of other brain mechanisms, as now illustrated.

Subcutaneous injection of the neurotoxin 5,7-dihydroxytryptamine (5,7-HT) in amounts of 50 mg/kg and within six hours after birth evokes a selective injury of the neural pathways containing serotonin (5-HT). Such lesions are typified by degeneration of the most distal parts of the serotoninergic neurones and subsequent denervation of the cerebral zone most distal to the cellular body. Following this rapid degenerative process there occurs a slow regeneration that in ca. 8–10 weeks results in the restoration of serotoninergic cerebral innervation. This regenerative process is preceded by a reactive phenomenon called the "pruning effect". The serotoninergic axons of the central nervous system are very long and bear mainly collateral branches. The first collateral branches break off at the level of the pons-medulla (where the serotoninergic cellular bodies are situated), whereas all other collateral branches break off further from the cellular body. Following neonatal injury with 5,7-HT the short axons innervating the ponsmedulla grow rapidly, giving rise to a reactive hyperinnervation of this zone. As the process of serotoninergic axonal regeneration proceeds, the so-called "pruning effect" is halted. In animals exposed perinatally to morphine as described above, this capacity for "pruning" is lacking; indeed, in such animals the serotoninergic neurones seem to be more sensitive to injury. Treatment with $T_4$ as described above re-establishes a normal "pruning effect", even in animals exposed to morphine. The data are listed in the following Table II.

TABLE II

| Levels of serotonin (ng/mg protein) in the pons-medulla 7 days after the neonatal lesion with 5,7-HT | | | |
|---|---|---|---|
| control | control + 5,7-HT | | |
| 18.8 ± 1.5 | 25.8 ± 2.8** | | |
| morphine | morphine + 5,7-HT | morphine + 5.7-HT + $T_4$ | |
| 16.2 ± 1.1 | 10.2 ± 0.7*** | 24.2 ± 1.9*** | |

These results therefore show that treatment with $T_4$ is able to restore the reactive plasticity of wounded neurones and the therapeutic advantage of using $T_4$ in the therapy of degenerative pathologies of the central nervous system such as Parkinsonism, Alzheimer's disease, trauma, etc. Such conclusions are confirmed by the fact that treatment with $T_4$ not only restores reactive plasticity of neurones of animals exposed to morphine, but also exerts a protective effect against degeneration, as indicated by reduced levels of serotonin in the pons-medulla of animals exposed to morphine and injured with 5,7-HT (see Table II).

EFFECT OF EXOGENOUS ADMINISTRATION OF $T_4$ ON COMPENSATORY NEUROCHEMICAL PHENOMENA IN THE RAT CORTEX

The perinatal administration of morphine, as described above, causes profound changes in the plasticity of the rat brain, as exemplified by the altered neurochemical development of the striated nucleus and by the reactive incapacity of cerebral serotoninergic neurones after neonatal lesions. As indicated above, the administration of $T_4$ corrects these alterations.

The following experiment was performed in order to confirm whether such changes in cerebral compensatory capacity in animals exposed perinatally to morphine extend to other neuronal systems and whether treatment with $T_4$ as per the above procedure restores the cerebral adaptive capacity. Pregnant rats were exposed as indicated above to increasing dosages of morphine immediately after birth, and within 6 hours the new-born rats were treated with a subcutaneous dose of 6-hydroxidopamine (6-OHDA). The latter substance is known for its typical neurotoxic properties, with high specificity for the catecholaminergic system, but when it was administered under our conditions the cerebral neurotoxic action was manifested exclusively against the noradrenergic system (NA). It was found that noradrenergic innervation of either the frontal or occipital cortex is destroyed or drastically reduced. Such reduction in noradrenergic innervation is permanent; in fact, the axons of these neurones can no longer re-establish themselves in their normal area of innervation in the cortex. Under these conditions, a compensatory neurochemical phenomenon has been established wherein lack of cerebral noradrenalin stimulates the compensatory growth of other neurotransmitter systems such as are reported in Table III. In this table we report that up to 8 weeks following the 6-OHDA-induced neonatal lesion the levels of noradrenalin in the frontal cortex are drastically reduced relative to the control values. A significant reduction is also observed in animals exposed perinatally to morphine. Reduced noradrenergic innervation stimulates a substantial rise in the levels of dopamine (DA), serotonin (5-HT) and metenkephalin (MET-ENK) in the frontal cortex of control animals treated with 6-OHDA, as shown in Table III. Perinatal exposure to morphine significantly alters these compensatory neurochemical processes. Indeed, as seen in Table III, despite noradrenergic denervation there is no evidence of compensatory processes from those parts of the dopaminergic, serotoninergic and metenkephalinergic systems. Therefore, perinatal exposure to morphine blocks the compensatory neurochemical phenomena of the cerebral cortex.

TABLE III

| Levels of neurotransmitters (ng/mg protein) in the frontal cortex 8 weeks after neonatal wounding with 6-xydroxidopamine | | | | |
|---|---|---|---|---|
| | NA | DA | 5-HT | MET-ENK |
| C | 7.0 ± 0.1 | 6.8 ± 1.0 | 22.6 ± 1.24 | 6.1 ± 0.7 |
| C + 6-OHDA | 2.8 ± 0.3** | 10.1 ± 0.9* | 36.2 ± 5.44** | 8.2 ± 0.6* |
| M | 6.3 ± 0.6 | 7.5 ± 0.9 | 22.7 ± 3.3 | 6.5 ± 0.6 |

TABLE III-continued

Levels of neurotransmitters (ng/mg protein) in the frontal cortex 8 weeks after neonatal wounding with 6-xydroxidopamine

|  | NA | DA | 5-HT | MET-ENK |
| --- | --- | --- | --- | --- |
| M + 6-OHDA | 2.9 ± 0.3** | 7.2 ± 0.3 | 22.3 ± 1.6 | 6.7 ± 0.4 |

C = control
M = rats exposed perinatally to morphine

When the animals from the various experimental groups are exposed perinatally to morphine and then treated with $T_4$ using the prescribed dosages and procedures, the aforementioned compensatory neurochemical processes develop normally, as indicated in Table IV.

TABLE IV

Levels of neurotransmitters (ng/mg protein) in the frontal cortex of control rats and rats exposed perinatally to morphine 8 weeks after neonatal wounding with 6-hydroxidopamine. The animals were treated with $T_4$ according to the aforementioned scheme.

|  | NA | DA | 5-HT | MET-ENK |
| --- | --- | --- | --- | --- |
| C | 7.2 ± 0.3 | 6.5 ± 0.4 | 21.5 ± 2.3 | 6.3 ± 0.3 |
| C + 6-OHDA | 2.3 ± 0.2** | 9.8 ± 0.2** | 33.5 ± 1.8** | 8.9 ± 0.4* |
| M | 6.8 ± 0.4 | 7.0 ± 0.2 | 22.8 ± 3.1 | 6.7 ± 0.3 |
| M + 6-OHDA | 1.8 ± 0.3** | 10.3 ± 0.5** | 32.6 ± 0.8** | 9.8 ± 0.6* |

C = control
M = rats exposed perinatally to morphine and treated with $T_4$

These data indicate that treatment with $T_4$ can restore cerebral compensatory reactive processes that would otherwise be altered in animals exposed perinatally to morphine (the latter compound being utilised as a means of experimentally inducing alterations in the intrinsic neuronal plasticity of the brain). Therefore, treatment with $T_4$ restores the phenomenon of plasticity, either when the reactive phenomena are directly due to neuronal lesions (developed in the striated nucleus, the "pruning effect" of the serotoninergic neurones), or when there is a neurochemical compensation involving various neurotransmitter systems that are not directly wounded.

We claim:

1. A method for stimulating neuronal plasticity in neuronal tissue which comprises administering a pharmaceutical composition comprising a pharmacology effective amount of thyroid $T_4$ to a patient in need thereof.

2. The method of claim 1, wherein said pharmaceutical composition is administered orally.

3. The method of claim 1, wherein said pharmaceutical composition is administered parenterally.

4. The method of claim 1, wherein said pharmaceutical composition comprises from 1 to about 100 mg thyroid hormone $T_4$ and a pharmacologically acceptable excipient.

5. The method of claim 1, wherein said patient is suffering from a degenerative pathology of the central nervous system.

* * * * *